United States Patent
Kolesnikov et al.

(10) Patent No.: US 7,700,122 B1
(45) Date of Patent: *Apr. 20, 2010

(54) TOPICAL COMPOSITIONS COMPRISING AN OPIOID ANALGESIC AND AN NMDA ANTAGONIST

(75) Inventors: Yuri Kolesnikov, Cresskill, NJ (US); Gavril W. Pasternak, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/806,645

(22) PCT Filed: Jul. 15, 1999

(86) PCT No.: PCT/US99/16049
§ 371 (c)(1), (2), (4) Date: Jul. 12, 2001

(87) PCT Pub. No.: WO00/03716
PCT Pub. Date: Jan. 27, 2000

Related U.S. Application Data

(60) Provisional application No. 60/092,982, filed on Jul. 16, 1998.

(51) Int. Cl.
*A61K 9/00* (2006.01)
*A61K 9/70* (2006.01)
*A61K 31/44* (2006.01)
*A61K 31/16* (2006.01)
*A61K 31/135* (2006.01)

(52) U.S. Cl. .......... 424/400; 424/449; 514/282; 514/647; 514/626

(58) Field of Classification Search .......... 424/401, 424/449, 400; 514/161, 282, 289, 647, 626
See application file for complete search history.

(56) References Cited

U.S. PATENT DOCUMENTS
5,322,683 A * 6/1994 Mackles et al. .......... 424/45
(Continued)

FOREIGN PATENT DOCUMENTS
JP 2000169378 6/2000
(Continued)

OTHER PUBLICATIONS
Lin et al "Long-term epidural ketamine, morphine and bupivacaine attenuate reflex symathetic dystrophy neuralgia," Can J. Anesth. Feb. 1998, vol. 45, No. 2, pp. 175-177.*
(Continued)

*Primary Examiner*—Shengjun Wang
(74) *Attorney, Agent, or Firm*—Edwards Angell Palmer & Dodge LLP; Peter C. Lauro; Mark D. Russett

(57) ABSTRACT

A topical opioid paradigm was developed to determine analgesic peripheral effects of morphine. Topical morphine as well as peptides such as [D-Ala2,MePhe4,Gly(ol)5]enkephalin (DAMGO) produced a potent, dose-dependent analgesia using the radiant heat tailflick assay. The topical drugs potentiated systemic agents, similar to the previously established synergy between peripheral and central sites of action. Local tolerance was rapidly produced by repeated daily topical exposure to morphine. Topical morphine tolerance was effectively blocked by the N-Methyl-D-Aspartate (NMDA) receptors antagonist MK801 and ketamine given either systemically or topically. NMDA receptor antagonists reversed preexisting morphine tolerance. The activity of topical NMDA antagonists to block local morphine tolerance suggests that peripheral NMDA receptors mediate topical morphine tolerance. Morphine was cross tolerant to [D-Ala2,MePhe4,Gly(ol)5]enkephalin (DAMGO), but not to morphine-6β-glucuronide, implying different mechanisms of action. These observations have great importance in the design and use of opioids clinically. Topical pharmaceutical compositions comprising an analgesic that functions through an opiate receptor and an NMDA receptor antagonist for producing analgesia without inducing tolerance are described.

13 Claims, 6 Drawing Sheets

U.S. PATENT DOCUMENTS

| | | | |
|---|---|---|---|
| 5,589,480 | A * | 12/1996 | Elkhoury et al. ............. 514/282 |
| 5,635,204 | A | 6/1997 | Gevirtz et al. |
| 5,840,731 | A * | 11/1998 | Mayer et al. ................. 514/289 |
| 5,849,761 | A * | 12/1998 | Yaksh ......................... 514/327 |
| 5,891,885 | A * | 4/1999 | Caruso ........................ 514/289 |
| 5,980,927 | A * | 11/1999 | Nelson et al. ................ 424/425 |
| 6,008,258 | A | 12/1999 | Inturrisi |
| 6,191,126 | B1 | 2/2001 | Gamache |
| 6,194,000 | B1 * | 2/2001 | Smith et al. .................. 424/458 |
| 6,261,582 | B1 * | 7/2001 | Needham et al. ............. 424/419 |
| 6,825,203 | B2 * | 11/2004 | Pasternak et al. ............ 514/282 |

FOREIGN PATENT DOCUMENTS

| | | |
|---|---|---|
| WO | WO 97/10815 | 3/1997 |
| WO | WO 98/26770 | 6/1998 |
| WO | WO 98/31358 | 7/1998 |
| WO | WO 00/03716 | 1/2000 |

OTHER PUBLICATIONS

Barber, A and Gottschlich, R. (1992) Opioid agonists and antagonists: an evaluation of their peripheral actions in inflammation. Med Res Reviews 12(5): 525-562.

Ben-Eliyahu, S., Marek, P. Vaccarino, AL, Mogil, JS, Sternberg, WF and Liebeskind, JC (1992) The NMDA receptor antagonist MK-801 prevents long-lasting non-associative morphine tolerance in the rat. Brain Res. 575: 304-308.

Brown, GP, Yang, K, King, MA, Rossi, GC, Levental, L, Chang, A. and Pasternak, GW (1997) 3-Methoxynaltrexone, a selective heroin.morphine-6 B-glucuronide antagonist. FEBS Lett 412: 35-38.

Carlton, SM, Hargett, GL and Coggeshall, RE (1995) Localization and activation of glutamate receptors in unmyelinated axons of rat glabrous skin. Neurosci Lett 197: 25-28.

Chien, C-C, Carroll, FI, Brown, GP, Pan, Y-X, Bowen, W and Pasternak, GW (1997) Synthesis and characterization of I-3'-iodopentazocrine, a selective , receptor ligand. Eur. J. Pharmacol. 321: 361-368.

Dahl, MR, Dasta, JF, Zuelzer, W. and McSweeney, TD (1990) Lidocaine local anesthesia for arthroscopic knee surgery. Anesth Analg 71: 670-674.

Dalsgaard, J, Felsby, S, Juelsgaard, p and Froekjaer, J. (1994) Low-dose intra-articular morphine anagesia in day case knee arthroscopy: A randomized double-blinded prospective study. Pain 56: 151-154.

Davidson, EM, Coggeshall, RE and Carlton, SM (1997) Peripheral NMDA and non-NMDA glutamate receptors contribute to nociceptive behaviors in the rat formalin test. Neuroreport 8(4): 941-946.

Gutstein, HB and Trujillo, KA (1993) MK-801 inhibits the development of morphine tolerance at spinal sites. Brain Res 626: 332-334.

Heard, SO, Edwards, T, Ferrari, D, Hanna, D, Wong, PD, Liland, A and Willock, MM (1992) Analgesic effect of intraarticular bupivacaine or morphine after arthroscopic knee surgery: a randomized, prospective, double-blind study. Anesth Analg 74: 822-826.

Joris, JL, Dubner, R and Hargreaves, KM (1987) Opioid analgesia at peripheral sites: a target for opioids released during stress and inflammation? Anesth Anal 66: 1277-1281.

Junien, JL and Wettstein, JG (1992) Role of opioids in peripheral analgesia. Life Sci 51(26): 2009-2018.

Khoury, GF, Chen, CAN, Garland, DE and Stein, C (1992) Intraarticular morphine, bupivacaine, and morphine/bupivacaine for pain control after knee videoarthroscopy. Anesthesiology 77: 263-266.

Kolesnikov, YA, Jain S, Wilson, R and Pasternak, GW (1996) Peripheral morphine analgesa: Synergy with Central sites and a target of morphine tolerance. J Pharmacol Exp Ther 279(2): 502-506.

Kolesnikov, Y.A. et al. "Peripheral blockade of topical morphine by Ketamine" European Journal of Pharmacology, 1999, 374/2.

Kolesnikov Y. et al. "Topical opioids in mice: Analgesia and reversal of tolerance by a topical N-methyl-D-aspartate antagonist" Journal of Pharmacology and Experimental Therapeutics, (1999) 290(1) 247-252.

Kolesnikov, YA , Pick, CG, Ciszewska, G and Pasternak, GW (1993) Blockade of tolerance to morphine but not to kappa opioids by a nitric oxide synthase inhibitor. Proc Natl Acad Sci USA 90: 5162-5166.

Mays, KS, Lipman, JJ and Schnapp, M. (1987) Local analgesia without anesthesia using peripheral perineural morphine injections. Anesth Analg 66: 417-420.

Pick, CG, Nejat, R and Pasternak, GW (1993) Independent expression of two pharmacologically distinct supraspinal Mu analgesic systems in genetically different mouse strains. J. Pharmacol. Exp. Ther. 265(1): 166-171.

Raja, SN, Dickenson, RE and Johnson, CA (1992) Comparison of postoperative analgesic effects of intraarticular bupivacaine and morphine following arthroscopic knee surgery. Anesthesiology 77: 1143-1147.

Reisine, T. and Pasternak, GW (1996) Opioid analgesics and antagonists. In goodman & Gilman's: The Pharmacological Basis of Therapeutics, ed. By JG Hardman and LE Limbird, pp. 521-556, McGraw-Hill.

Roerig, SC, O'Brien, SM, Fujimoto, JA and Wilcox, GL (1984) Tolerance to morphine analgesia: decreased multiplicative interaction between spinal and supraspinal sites. Brain Res. 308: 360-363.

Rossi, GC Brown, GP, Leventhal, L. Yang, and Pasternak, GW (1996) Novel Receptor mechanisms for heroin and morphine glucuronide analgesia. Neurosci Lett 216: 1-4.

Stein, C., Schafer, M. and Hassan, AHS (1995) Peripheral opioid receptors. Ann. Med. 27: 219-221.

Trujillo, KA and Akil, H. (1994) Inhibition of opiate tolerance by non-competitive N-methyl-D-aspartate receptor antagonists. Brain Res 633: 178-188.

Zhou, S, Bonasera, L. and Carlton, SM (1996) Peripheral administration of NMDA, AMPA or KA results in pain behaviors in rats. Neuroreport 7: 895-900.

Kolesnikov Yuri A et al. "Analgesic synergy between topical lidocaine and topical opioids" Journal of Pharmacology and Experimental Therapetics, vo. 295, No. 2, Nov. 2000 pp. 546-551, XP 001080389.

Khoury G F et al. "Intraarticular Morphine, Bupivacaine, and Morphine/Bupivacaine for pain control after knee videoarthroscopy" Anesthesiology, American Society of Anesthesiologists, Philadelphia, PA, US, vol. 77, No. 263, 1992, pp. 263-266, XP000910063.

Kaneko Megumi et al. "Synergistic antinociceptice interaction after epidural coadministratio of morphine and lidocaine in rats." Anesthesiology, vol. 80, No. 1, 1994, pp. 137-150, XP001080405.

Saito Yoji et al. "Interaction of intrathecally infused morphine and lidocaine in rats (Part 1)." Anesthesiology (Hagerstown), vol. 89, No. 6, Dec. 1998 pp. 1455-1463, XP001080402.

Atanassoff Peter G et al. "The effect of intradermal administration of lidocaine and morphine on the response to thermal stimulation." Anesthesia & Analgesia, vol. 84, No. 6, 1997, pp. 1340-1343, XP001079098.

Leopold, C. et al., "Percutaneous Penetration of Local Anasthetic Bases: Pharmacodynamic Measurements," *J. of Invest. Dermatol.*, 113(3): 304-307, 1999.

Picard, P. et al, "Analgesic efficacy of peripheral opioids (all except intra-articular): a qualitative systematic review of randomized controlled trials," *Pain*, 72: 309-318, 1997.

Raja, S. et al., "Comparison of postoperative analgesic effects of intraarticular bupivacaine and morphine following arthroscopic knee surgery," *Anesthesiology*, 77(6): 1143-47, 1992.

Rosenstock, C. et al., "Analgesic effect of incisional morphine following inguinal hemiotomy under spinal anesthesia," *Regional Anesthesia*, 21(2): 93-98, 1996.

Roy, S.D. et al., "Transdermal Delivery of Narcotic Analgesics: Comparative Permeabilities of Narcotic Analgesics Through Human Cadaver Skin," *Pharmaceutical Research*, 6(10): 825-832, 1989.

Roy, S.D. et al., "Transdermal Delivery of Narcotic Analgesics: Comparative Metabolism and Permeability of Human Cadaver Skin and Hairless Mouse Skin," *Journal of Pharmaceutical Sciences*, 83(12): 1723-28, 1994.

Yarussi, A. et al., "Evaluation of peripheral morphine analgesia for lumpectomy and axillary node dissection: a randomized, double-blind, placebo-controlled study," *Reg. Anasth. Pain Med.*, 24(2): 142-145, 1999.

Moore, U.J. et al. "The efficacy of locally applied morphine in post-operative pain after bilateral third molar surgery," Br. J. Clin. Pharmac. 37:227-30, 1994.

Picard, P. et al., "Analgesic efficacy of peripheral opioids (all except intra-articular): a qualitative systematic review of randomized controlled trials," Pain, 72: 309-318, 1997.

Raja, S. et al., "Comparison of postoperative analgesic effects of intraarticular bupivacaine and morphine following arthroscopic knee surgery," Anesthesiology, 77(6):1143-47, 1992.

Rosenstock, C. et al., Analgesic effect of incisional morphine following inguinal herniotomy under spinal anesthesia, Regional Anesthesia, 21(2):93-98, 1996.

Roy, S.D. et al., "TransdermalDelivery of Narcotic Analgesics: Comparative Permeabilities of Narcotic Analgesics Through Human Cadaver Skin," Pharmaceutical Research, 6(10): 825-832, 1989.

Roy, S.D. et al., "Transdermal Delivery of Narcotic Analgesics: Comparative Metabolism and Permeability of Human Cadaver Skin and Hairless Mouse Skin," Journal of Pharmaceutical Sciences, 83(12) 1723-28, 1994.

Yarussi, A. et al., "Evaluation of peripheral morphine analgesia for lumpectomy and axillary node dissection: a randomized, double-blind, placebo-controlled study," Reg. Anasth. Pain Med., 24(2): 142-145, 1999.

Leopold et al. "Percutaneous Penetration of Local Anesthetic Bases: Pharmacodynamic Measurements" The Journal of Investigative Dermatology 113(3) 304-307 (1999).

T. Buffington, "Visceral Pain in Humans: Lessons from Animals", Current Pain and Headache Reports 2001, 5:44-52,Current Science Inc. ISSN 1531-3433, pp. 44-51.

J. Deleo, "Basic Science of Pain", The Journal of Bone and Joint surgery, Inc., 10/04/26, pp. 57-62.

D, Le Bars, et al., "Animal Models of Nociception", Pharmacological Reviews, The American Society for Pharmacology and Experimental Therapeutics, 2001, vol. 53, No. 4, USA, pp. 597-652.

Final Office Action dated Oct. 21, 2009, from co-pending U.S. Appl. No. 10/823,365.

* cited by examiner

TOPICAL COMPOSITIONS COMPRISING AN OPIOID ANALGESIC AND AN NMDA ANTAGONIST

This application claims priority to provisional U.S. application Ser. No. 60/092,982 filed Jul. 16, 1998 which is incorporated herein by reference in its entirety.

This invention was made with government support under Grant Number DA07242, DA00220 and CA08748 awarded by The National Institutes of Health. The U.S. government has certain rights in the invention.

FIELD OF THE INVENTION

The invention is directed to topical pharmaceutical compositions of an N-methyl-D-aspartate receptor antagonist alone or in combination with an analgesic that functions through an opiate receptor for peripheral analgesia and uses of the topical pharmaceutical compositions for treatment of pain, with no/or minimal tolerance development to the analgesic.

BACKGROUND OF THE INVENTION

Morphine is a potent mu opioid receptor agonist with important central sites of action (Reisine and Pasternak, 1996). Peripheral mechanisms also have been reported and their importance is becoming increasing appreciated (Stein et al., 1995; Barber and Gottschlich, 1992; Joris et al., 1987; Junien and Wettstein, 1992). Peripheral analgesics have a number of potential advantages in the clinical treatment of pain, particularly the limitation of side-effects such as constipation and sedation which are typically seen with systemic administration. Given locally into the tail, morphine and other opioids are effective analgesics, working either alone peripherally or synergistically at central sites (Kolesnikov et al., 1996). In many respects, these studies are similar to clinical investigations (Stein, 1993; Dahl et al., 1990; Dalsgaard et al., 1994; Heard et al., 1992; Joris et al., 1987; Khoury et al., 1992; Mays et al., 1987; Raja el al., 1992). Peripheral mechanisms also have been implicated in systemic morphine tolerance (KQlesnikov et al., 1996). Early studies reported that systemic morphine tolerance does not alter the sensitivity to morphine given either spinally or supraspinally (Roerig et al., 1984). Although we also found potency to remain unchanged for spinal or supraspinal morphine following chronic morphine dosing, a profound reduction in its potency peripherally was observed (Kolesnikov et al., 1996).

SUMMARY OF THE INVENTION

The present invention relates to method and compositions for providing topically administered N-methyl-D-aspartate (NMDA) receptor antagonists to obtain more efficient peripheral analgesia using an analgesic that functions through an opiate receptor and for tolerance inhibition and/or tolerance reversal to the analgesic.

The present invention provides a topical pharmaceutical composition comprising an N-methyl-D-aspartate receptor antagonist alone or in combination with at least one analgesic that functions through an opiate receptor and a pharmaceutically acceptable topical excipient.

Another aspect of the invention is a method of providing analgesia to a mammal comprising systemic or topical administration of an analgesic that functions through an opiate receptor, and which analgesic is administered before, with, or following the topical administration to the mammal of a tolerance-reducing or tolerance-inhibiting amount of at least one N-methyl-D-aspartate receptor antagonist.

Another aspect of the invention is a method of reversing tolerance in a mammal treated with an analgesic that functions through an opiate receptor comprising the topical administration of an effective tolerance-reversing amount of at least one NMDA receptor antagonist.

The present invention further provides a pharmaceutical tolerance-reducing or tolerance-inhibiting analgesic kit comprising:

(A) a topical or systemic pharmaceutical composition comprising at least one analgesic that functions through an opiate receptor; and (B) a topical pharmaceutical composition comprising at least one tolerance-reducing or tolerance-inhibiting N-methyl-D-aspartate receptor antagonist.

1a) Groups of mice received a 2 min topical exposure to morphine (15 mM; n=20), DAMGO (2 mM; n=10) or M6G (20 mM; n=10) and were tested in the tailflick assay.

1b) Dose-response curves were generated for each of the designated compounds applied topically for 1 min, as described in Methods. Each dose of drug had at least 10 mice/group.

Figure 2A:
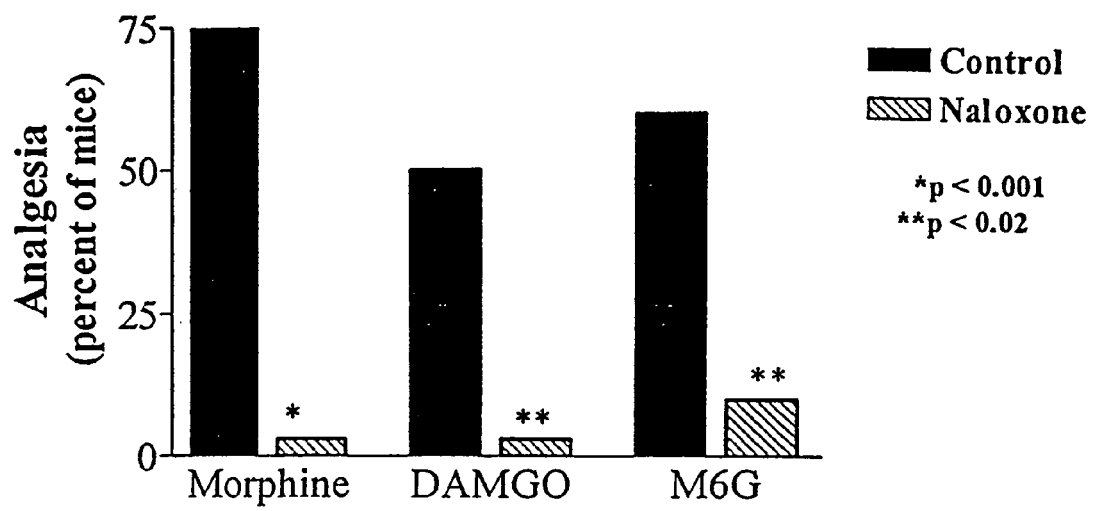
Figure 2B:
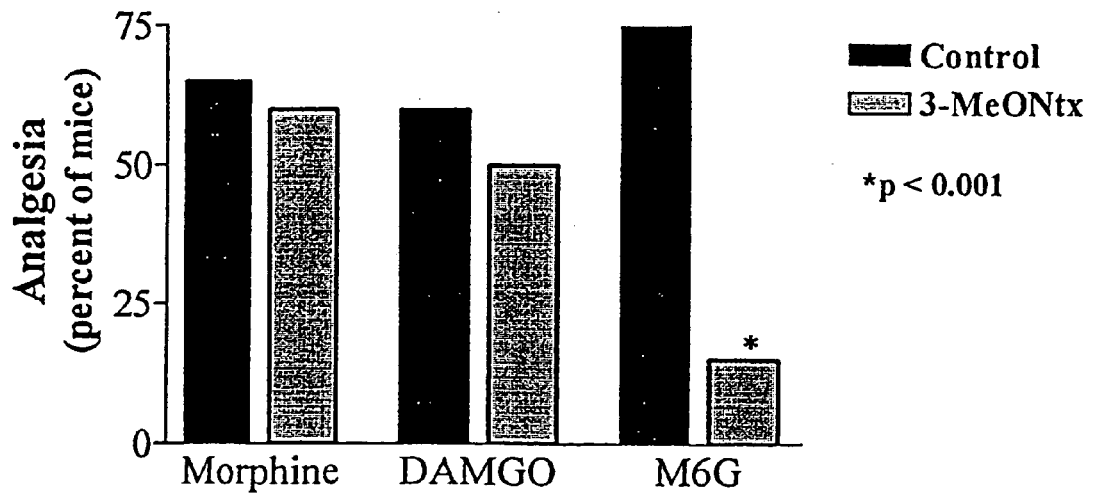

FIGS. 2a and 2b: Effects of opioid antagonists on topical Mu analgesia

2a) Groups of mice (n≧10) received either morphine (15 mM), DAMGO (2 mM) or M6G (20 mM) topically for 1 min alone or with naloxone (1 mg/kg, s.c.) injected subcutaneously on the back 20 min prior to the analgesic agonists. Naloxone, a Mu receptor antagonist, significantly reduced the responses for all agonists.

2b) Groups of mice (n≧10) received either morphine (15 mM), DAMGO (2 mM) or M6G (20 mM) topically for 1 min alone or with 3-methoxynaltrexone (3-MeONtx; 0.25 mg/kg, s.c.) injected subcutaneously on the back 20 min prior to the agonists. 3-MeONtx significantly lowered the response only for M6G.

Figure 3A:
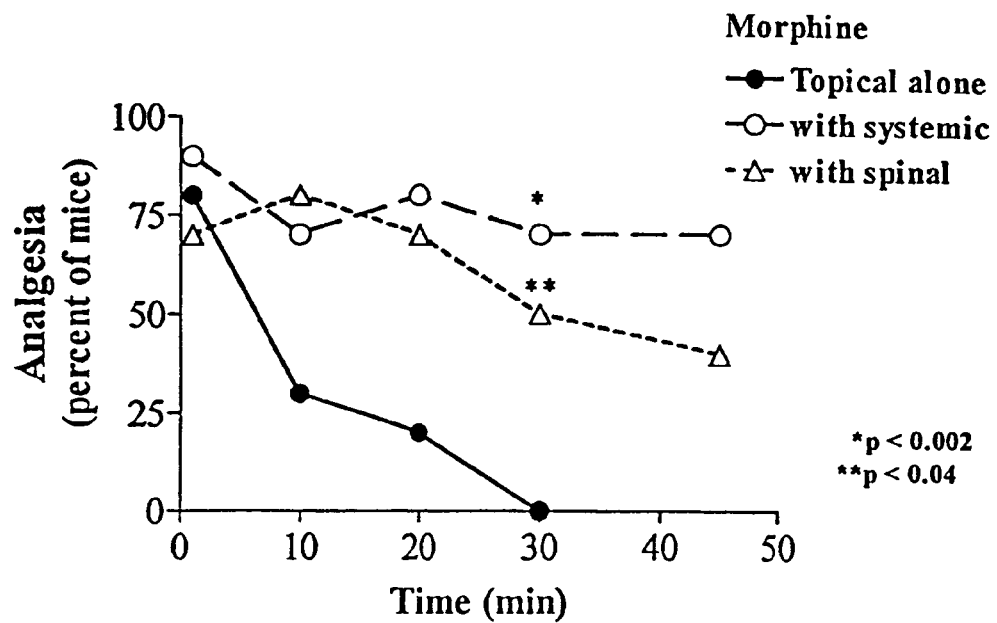
Figure 3B:
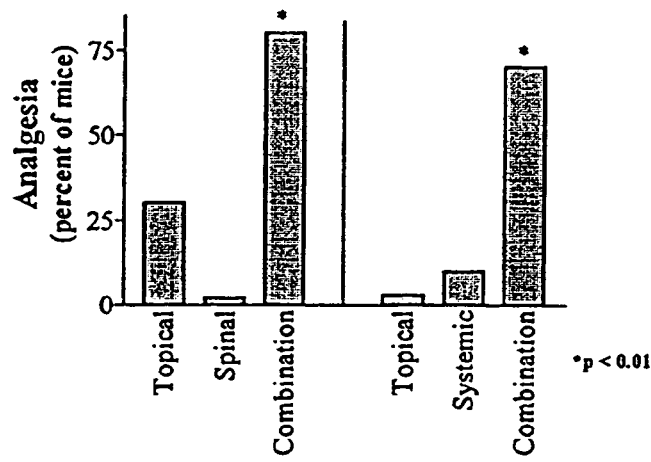

FIGS. 3a and 3b: Interactions between topical and either systemic or spinal morphine 3a) Groups of mice (n≧10) received topical morphine (15 mM; 2 min) alone, or with spinal (100 ng, i.t.) or systemic (1 mg/kg, s.c.) morphine. The spinal morphine dose alone had no observable action and the systemic dose produced only a 10% response. At 30 min, when the response to topical drug alone was lost, the responses of the combinations were significantly greater.

3b) Left: Groups of mice (n≧10) received topical morphine (15 mM; 2 min) alone, spinal morphine (100 ng, i.t.) alone or both together. Testing was performed 10 min following drug administration. At this time point, topical morphine alone had a 30% response. The combined dosing was significantly more active than the sum of the two individual routes alone. Right: Groups of mice (n≧10) received topical morphine (15 mM) alone, systemic morphine (1 mg/kg, s.c.) alone or both together. Testing was performed 30 min following drug administration. At this time point, topical morphine alone had no observable response. The combined dosing was significantly greater than the sum of the two ones alone.

Figure 4:
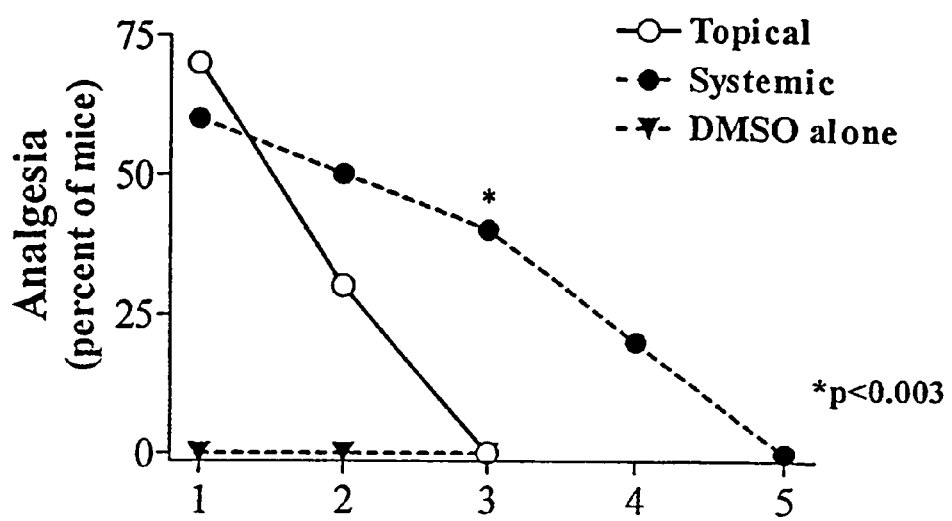

FIG. 4: Tolerance to systemic and topical morphine

Groups of mice (n≧10) received either morphine systemically (5 mg/kg, s.c.) or topically (15 mM; 1 min). DMSO alone had no observable effect on days 1, 2 or 3. On day 3, the response in the systemic group was significantly greater than the topical group.

Figure 5:
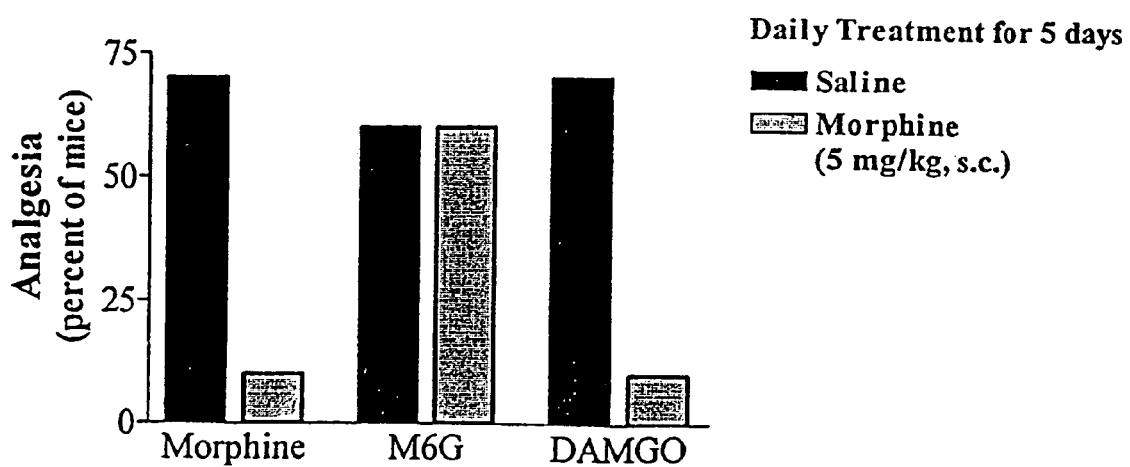

FIG. 5: Cross tolerance between morphine and DAMGO and M6G

Groups of mice (n≧10) received morphine (5 mg/kg, s.c.) or saline daily for five days. On the sixth day, the mice were tested after local exposure (1 min) to morphine (15 mM), M6G (20 mM) or DAMGO (2 mM). The response to morphine and DAMGO after chronic morphine treatment was significantly decreased (p<0.01). There was no change in the response to M6G.

Figure 6A:
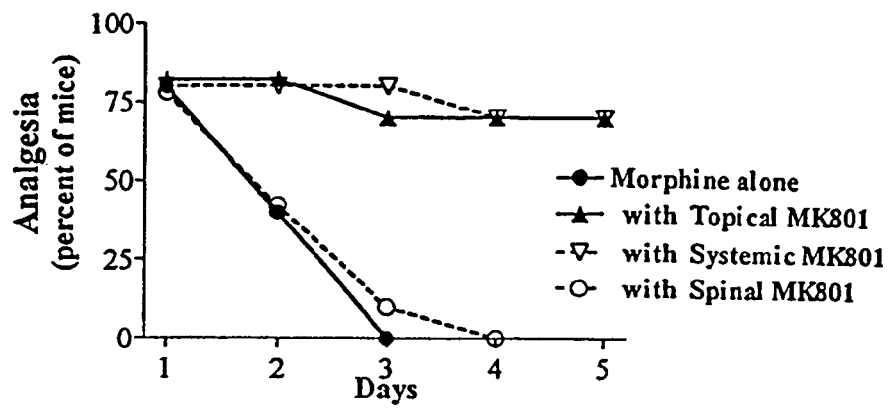
Figure 6B:
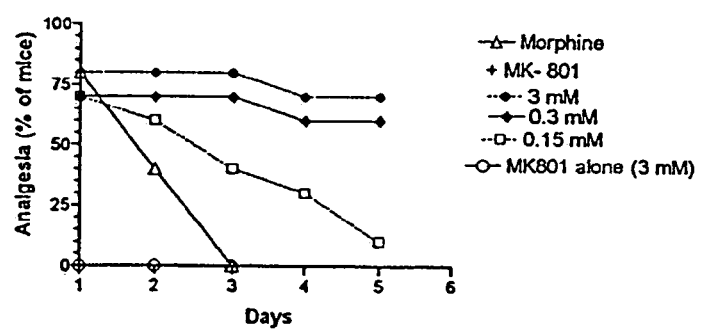
Figure 6C:
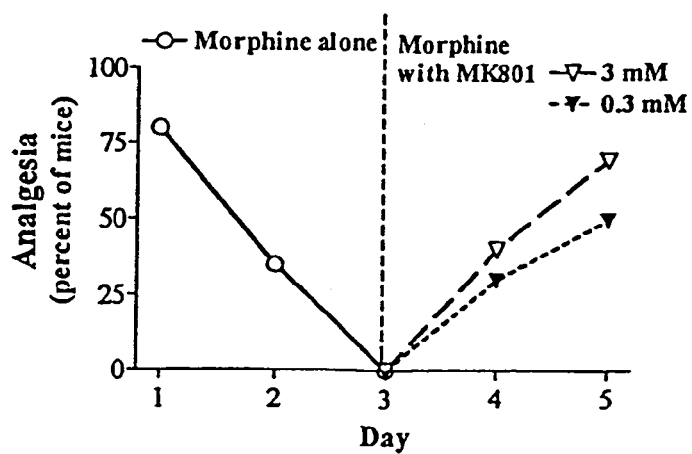

FIGS. 6a, 6b and 6c: Effects of MK801 on topical morphine tolerance

6a) Groups of mice (n≧10) received topical morphine (15 mM; 1 min) alone or with MK801 given either topically (3 mM), systemically (0.1 mg/kg, s.c.) or intrathecally (1 µg, i.t.). After three days the response to morphine alone was lost (p<0.01), as was the response to morphine with intrathecal MK801 (p<0.01). The combination of morphine with either systemic or topical MK801 remained essentially unchanged for five days.

6b) Groups of mice (n≧10) received topical morphine (15 mM; 1 min) alone, topical MK801 alone (3 mM) or topical morphine (15 mM) with topical MK801 at the indicated concentration (0.15, 0.3 or 3 mM). After three days, the response to morphine alone was lost (p<0.01). The two higher MK801 doses prevented the loss of responsiveness (p<0.01) while the lowest doses gave an intermediate response.

6c) Groups of mice (n≧10) received topical morphine (15 mM; 1 min) alone for three days. Starting on the fourth day, they received topical morphine with topical MK801 at either 0.3 or 3 mM. Coadministration of topical MK801 with topical morphine reversed the previously established tolerance (p<0.01).

Figure 7:
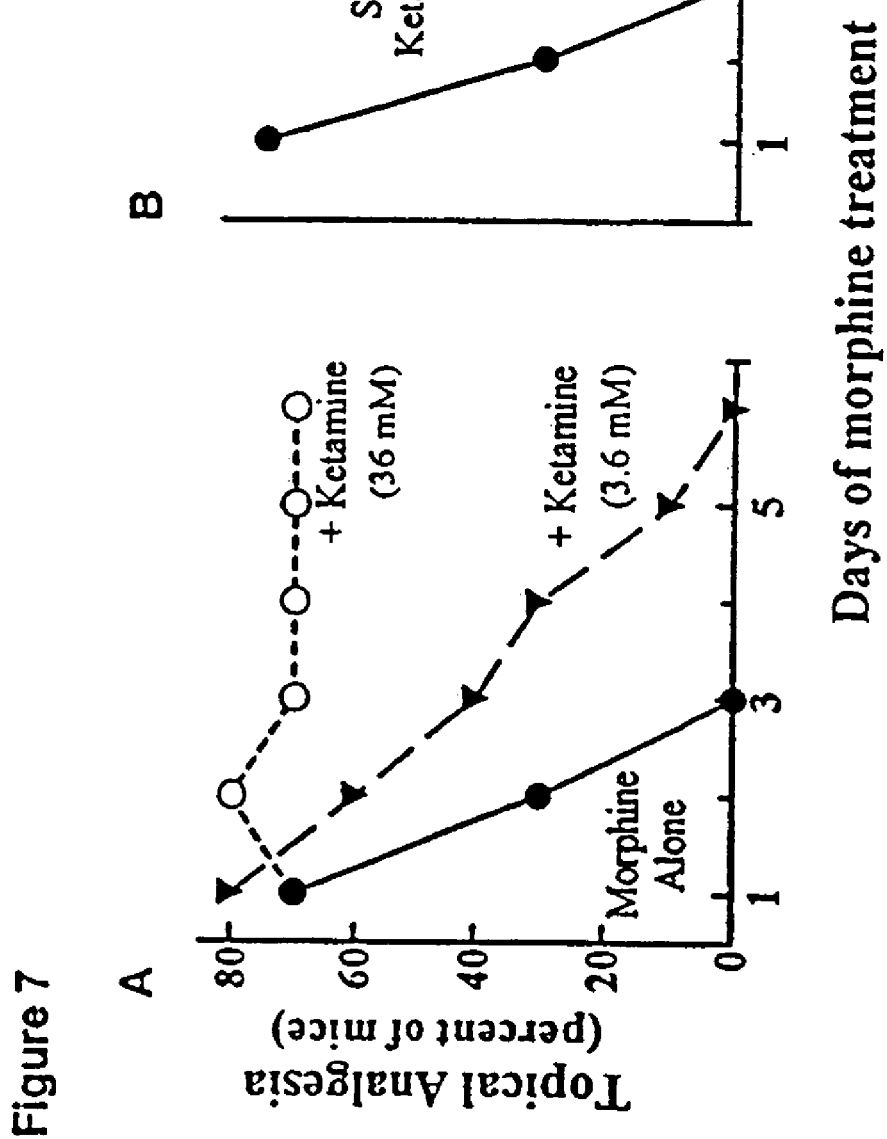

FIGS. 7a and b: Effect of ketamine on topical morphine tolerance

7a: Groups of mice (n=20) were treated topically once daily for 3 days with morphine (15 mM) alone (closed circles) or both morphine with ketamine at 3.6 mM (triangles) or 36 mM (open circles). Ketamine alone (36 mM) did not produce significant analgesia in this model. After three days, the response to morphine alone was lost (p<0.001). The lower ketamine dose (3.6 mM) significantly lessened the loss of morphine analgesic response after three days (p<0.05). The higher ketamine dose (36 mM) prevented tolerance up to six days (p<0.0001).

7b. Groups of mice (n=20) received topical morphine (15 mM) alone (closed circles) for two days. Starting on the day 3, the two groups of mice received daily doses of morphine in conjunction with either ketamine at either 3.6 (triangles) or 36 mM (squares) through day 6. The higher ketamine dose (36 mM) completely restored morphine analgesia (p<0.0001).

DETAILED DESCRIPTION OF THE INVENTION

The present invention provides a topical pharmaceutical composition comprising of at least one N-methyl-D-aspartate (NMDA) receptor antagonist alone or in combination with at least one analgesic that functions through an opiate receptor and a pharmaceutically acceptable topical excipient.

N-methyl-D-aspartate receptor antagonists for use in the present invention include but are not limited to morphinans such as dextromethorphan ((+)-3-hydroxy-N-methylmorphinan) and dextrorphan ((+)-3-hydroxy-N-methylmorphinan), MK-801 ((5R,10S)— (+)-5-methyl-10,11-dihydro-5H-dibenzo[a,d]cyclohapten-5,10-immine hydrogen maleate), ketamine (2-(2-chlorophenyl)-2-(methylamino) cyclohexanone), pyroloquinoline quinone and cis-4-(phosphonomethyl)-2-piperidine carboxylic acid, memantine (3,5-dimethyl-9-adamantanamine hydrochloride), their mixtures and the pharmaceutically acceptable salts thereof, and the like. Except for dextromethorphan, many current NMDA receptor antagonists have not been suitable for systemic clinical use due to profound psychomimetic side effects. Such NMDA receptor antagonists, however, may be used in the present invention in topical formulations. Topical use of these NMDA receptor antagonists allows for interference and attenuation of tolerance development to analgesics without producing limiting side effects. NMDA receptor antagonists that may be used in topical formulations include but are not limited to MK 801, dextromethorphan, ketamine, memantine, dextrophan, their mixtures and pharmaceutically acceptable salts thereof, pyroloquinoline quinone, cis-4-(phosphono-methyl)-2-piperidine carboxylic acid, their mixtures and pharmaceutically acceptable salts thereof, and the like.

Analgesics which may be used in the present invention are those that provide analgesia through activation of at least one type of opiate receptor. The opiate receptors that may be activated by the analgesic component of the present invention include but are not limited to any one or combination of delta (δ) opiate receptors, kappa (κ) opiate receptors and Mu opiate receptors. The analgesics include but are not limited to opiates, opiate derivatives, and synthetic opioids, endogenous or synthetic opioid peptides such as enkephalins, endorphins and their pharmaceutically acceptable salts. Specific examples include ethylmorphine, hydromorphone, morphine, codeine, oxymorphone, [D-Ala$^2$, MePhe$^4$, Glycol)$^5$] enkephalin (DAMGO), propoxyphene, buprenorphine, oxycodone, hydromorphone, hydromorphine, fentanyl, sufentanil, pentazocine, nalbuphine, nalorphine, heroin, levorphanol, levallorphan, methadone, meperidine, cocaine, dihydrocodeine, hydrocodone, nalmefene, naloxone, naltrexone, butorphanol, and the pharmaceutically acceptable salts and the like.

Optionally, the topical pharmaceutical composition of the present invention may further comprise a local anesthetic including but not limited to lidocaine, bupivacaine, meprivacaine, ropivacaine, tetracaine, benzocaine and the like.

As used herein, a mammal that may benefit from the methods of treatment of the present invention is any warm-blooded animal in need of treatment for pain. Mammals include but are not limited to humans, primates, dogs, cats, rodents, horses, cattle, sheep, and the like. The analgesic is provided to a mammal in need of relief from pain. The pain may be an acute or chronic pain. Diseases or conditions which may necessitate analgesia include but are not limited to pain associated with trauma, amputation, neuropathy, fibromyalgia, burns, abrasions, infections, lacerations, incisions and the like.

This invention provides for attenuating or preventing the development of tolerance associated with the administration of narcotic analgesics. Accordingly, NMDA receptor antagonists may be administered in amounts which are effective for either attenuating or preventing tolerance development. As used herein, the term tolerance preventing, tolerance-inhibiting or tolerance-reversing dose is an amount of an NMDA receptor antagonist effective to maintain and/or restore, or at least partially restore, the analgesic effect of the narcotic analgesic.

In a method of providing peripheral analgesia to a mammal, a tolerance-attenuating or preventing dose of at least one NMDA receptor antagonist is administered topically prior to, concurrently or following topical administration of at least one analgesic that functions through an opiate receptor.

In one embodiment of the method of providing analgesia to a mammal, a tolerance-attenuating or inhibiting dose of the NMDA receptor antagonist, ketamine is administered topically prior to, concurrently or following topical administration of the opiate analgesic, morphine.

In another embodiment of the method of providing analgesia to a mammal, a tolerance inhibiting or tolerance-reversing dose of the NMDA receptor antagonist, dextromethorphan, is administered topically prior to, concurrently or following topical administration of the opiate analgesic, morphine.

Administration of a topical pharmaceutical composition of the invention may be in the form of a single dosage unit comprising the NMDA receptor antagonist alone or in combination with the analgesic in a topical formulation in effective amounts.

The concentration of the topical NMDA receptor antagonist in the pharmaceutical composition is in a range of about 0.1% to about 5% by weight in mixture but may vary in amounts depending on particular antagonist used and the particular analgesic being administered to the mammal. The concentration of the topical NMDA receptor antagonist provides a dose-lowering effect on the concentration of analgesic needed to provide effective analgesia. For example, a concentration of analgesic, when used in combination with a topical NMDA receptor antagonist may be provided in a range of about 1.0 to about 10% by weight for topical administration of the analgesic, in a range of about 0.1 to about 0.2 mg/kg body weight for systemic administration of the analgesic and in a range of about 1-5 mg for intrathecal administration of the analgesic.

A particular dose of the topical composition may be provided for example, 2-3 times per day, or any period sufficient to prevent, inhibit or reverse tolerance in the mammal receiving an analgesic that functions through an opiate receptor.

The topical pharmaceutical compositions may be formulated as an aqueous solution, lotion, gel, cream ointment, adhesive film and the like, with pharmaceutically acceptable excipients such as aloe vera, propylene glycol, DMSO, lecithine base, and the like. DMSO, as used in the present invention, does not provide systemic adsorption of the therapeutic. A gel excipient may comprise one or more of the following—petrolatum, lanoline, polyethylene glycols, bee wax, mineral oil, diluents, such as water and alcohol, and emulsifiers and stabilizers.

Aqueous suspensions can contain the composition in admixture with pharmaceutically acceptable excipients such as suspending agents, e.g., sodium carboxymethyl cellulose, methylcellulose, hydroxypropylmethylcellulose, sodium alginate, polyvinylpyrrolidone, gum tragacanth and gum acacia; dispersing or wetting agents such as naturally occurring phosphatide, e.g., lecithin, or condensation products of an alkylene oxide with fatty acids, e.g., polyoxyethylene stearate, or condensation products of ethylene oxide with long chain aliphatic alcohols, e.g., heptadecaethyleneoxycetanol, or condensation products ethylene oxide with partial esters derived from fatty acids and a hexitol, e.g., polyoxyethylene sorbitol monoleate or condensation products of ethylene oxide with partial esters derived from fatty acids and hexitol anhydrides, e.g., polyoxyethylenes sorbitan monooleate. Such aqueous suspensions can also contain one or more preservatives, e.g., ethyl or n-propyl-p-hydroxy benzoate.

Dispersible powders and granules suitable for preparation of an aqueous suspension by the addition of water provide the composition in admixture with a dispersing or wetting agent, suspending agent and one or more preservatives. Suitable dispersing or wetting agents and suspending agents are exemplified by those already mentioned above.

The composition of this invention or either of its principal active ingredients can be provided in sustained release dosage formulations as are known in the art.

A topical formulation of the present invention delivers a therapeutic effect on the peripheral opiate receptors and is not required to deliver the active ingredients in the topical formulation to central (brain and spinal cord) opiate receptors. The topical formulations of the present invention provides local delivery of the active ingredients and is not required to provide systemic delivery of the active ingredients in the formulation in the treated mammals.

Topical administration of the pharmaceutical composition may be accomplished by application of a solution, gel, lotion, ointment, cream or other vehicle topically used to deliver therapeutics to a local site. One means of application is by spraying the composition over the area to be treated. In another embodiment, a patch which provides a sustained release topical formulation may also be used to administer the topical therapeutic. The patch may be a reservoir and porous membrane type or a solid matrix as are known in the art. The active agents may be in a plurality of microcapsules distributed throughout the permeable adhesive layer.

In another embodiment of the method of providing analgesia to a mammal with pre-existing tolerance to an analgesic, a tolerance-reversing dose of at least one NMDA receptor antagonist is topically administered concurrently or following topical or systemic administration of at least one analgesic that functions through an opiate receptor.

The pharmaceutical composition of the NMDA receptor antagonist for topical administration may also be provided in kit form, along with at least one topical or systemic pharmaceutical composition comprising an analgesic that functions through an opiate receptor.

The present invention also encompasses a method of providing analgesia to a mammal comprising topical administration of at least one analgesic that functions through an opiate receptor prior to, concurrently, or following systemic or intrathecal administration of at least one analgesic. The combination of topical administration with systemic or intrathecal administration of the analgesic provides effective and therapeutic analgesia at low doses of the topical analgesic and low doses of systemic or intrathecal analgesic with concommittant lowering of detrimental side-effects of the analgesic. The doses used in the combination therapy are doses that are lower than the dose required to achieve a therapeutic level of analgesia using either analgesic, alone. The concentration of the topical analgesic in a pharmaceutical composition, for use in the combination analgesic therapy is in a range of about 1 to about 10% by weight. The concentration of the systemic analgesic in a pharmaceutical composition for use in the combination analgesic therapy is in range as so to provide about 0.1 to about 0.2 mg/kg body weight. In the case of intrathecal administration of an analgesic, in combination with a topical analgesic, the concentration of the intrathecal analgesic is in a range of about 1 to about 5 mg. The therapy may be supplemented by administration of a tolerance-attenuating or tolerance-preventing dose of at least one topical NMDA receptor antagonist. The topical NMDA receptor antagonist may be provided in a concentration range of about 0.1% to about 5% by weight of the formulation.

In one embodiment of a method of providing analgesia to a mammal, topical morphine is administered prior to, concurrently or following systemic or intrathecal administration of morphine.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments.

All references and patents referred to are incorporated herein by reference.

EXAMPLE 1

Materials and Methods

Male Crl:CD-1(ICR)BR mice (25-30 g; Charles River Breeding Laboratories, Bloomington, Mass.) were maintained on 12-h light/dark cycle with food and water available ad libitum. Mice were housed in groups of five until testing. [$^{125}$I]NaI (1680 Ci/mmol) was purchased from New England Nuclear (Boston, Mass.). Morphine, morphine-6β-glucuronide (M6G) and [D-Ala$^2$,MePhe$^4$,Gly(ol)$^5$]enkephalin (DAMGO) were generously provided by the Research Technologies Branch of National Institute on Drug Abuse (Rockville, Md.). MK801 was purchased from Research Biochemicals, Inc. (Natick, Mass.).

Systemic drugs were given subcutaneously (s.c.) in the midscapular region of the back. Intracerebroventricularly (i.c.v.) and intrathecal injections were performed under light halothane anesthesia 30 and 15 min before testing, respectively, as previously reported (Kolesnikov et al, 1996). The i.c.v. injections were administered-2 mm caudal and 2 mm lateral to the bregma at a depth of 3 mm, whereas intrathecal injections were made by lumbar puncture. Drugs were given topically on the tail by immersion of the tail in dimethylsulfoxide (DMSO) solutions containing the indicated drugs. The distal portion of the tail (3 cm) was immersed in DMSO solution for 1 min. Tailflick latencies then were determined on the region of the tail immersed in the drug, unless otherwise stated. To ensure a local effect, testing was also done with a more proximal segment of tail not exposed to the drug solution.

Analgesia was assessed with the tail-flick assay, as previously reported (Kolesnikov et al., 1996). The tail was exposed to a focused beam of light and the latency of exposure determined. Base-line latencies ranged from 2.5 to 3.5 sec. A maximum cutoff latency of 10 sec was used to minimize tissue damage in analgesic animals. Testing was performed 30 min after systemic administration, 15 min after either i.c.v or i.t. injections or immediately after termination of topical administration into the tail. Antinociception, or analgesia, was defined quantally as a tailflick latency for an individual mouse which was at least twice its baseline latency. Group comparisons were performed using the Fisher exact test. $ED_{50}$ values were determined using the Bliss program, as previously reported (Pick et al., 1993). To ensure a local action, in all studies we examined a region of the tail which was immersed in DMSO as well as a more proximal segment which was not exposed. Tailflick latencies from the unexposed portion of the tail were similar to base line latencies. DMSO itself had no activity in this model. Testing regions of the tail exposed and not exposed to the DMSO revealed no significant antinociceptive effect in either location.

[$^{125}$I]Morphine and [$^{125}$I]DAMGO were synthesized at room temperature using the chloramine T method with equimolar amounts of [$^{125}$]NaI and either morphine or DAMGO. The reaction terminated with sodium metabisulfite after 1 minute and the radiolabeled opioid separated from unreacted N $^{125}$I by a C18-reverse phase SepPak (Chien et al., 1997). The radiolabeled compounds were not further separated from the non-iodinated precursors.

EXAMPLE 2

Topical Morphine and DAMGO Analgesia

Figure 1A:
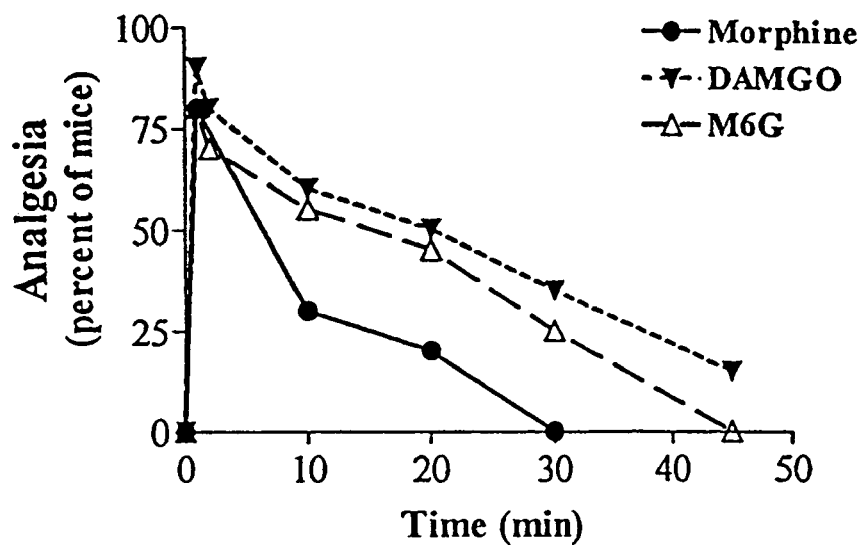
FIGS. 1a and 1b: Topical opioid analgesia in the mouse
Figure 1B:
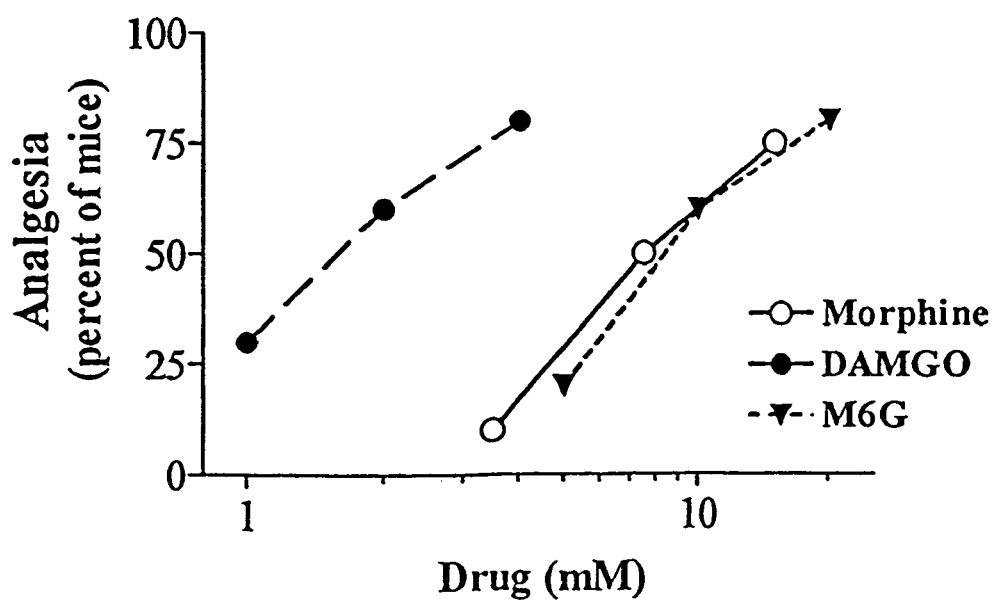

Prior studies from our group demonstrated a potent local analgesic activity of morphine administered subcutaneously in the tail (Kolesnikov et al., 1996). Morphine also was a potent analgesic when applied topically. The analgesic response to a morphine solution (7.5 mM) progressively increased over time, going from only 25% after 30 seconds to 50% by one minute and 80% after 2 min (data not shown). The onset of the response was quite rapid. Analgesia was detectable within one minute after removal of the tail from the opioid solution, the shortest time tested (FIG. 1a). However, the duration of the morphine response was relatively brief, typically lasting less than 30 min. Using a fixed exposure time, morphine produced a dose-dependent effect (FIG. 1b; Table 1). Similar results were observed with DMSO solutions of the mu opioid peptide DAMGO, which was over 5-fold more potent (FIG. 1b; Table 1).

TABLE 1

Analgesic activity of topical opioids in CD-1 mice

| Opioids | $ED_{50}$ (95% CL) | Relative potency |
| --- | --- | --- |
| Morphine | 8.3 mM (4-13) | 1 |
| M6G | 9.3 mM (7-14) | 0.9 |
| DAMGO | 1.6 mM (1-2.5) | 5 |

Analgesic $ED_{50}$ values with 95% confidence limits were determined using at least three doses of drug in groups of mice ( n 10-20/dose) in the tailflick assay. All drugs were administered topically for 1 mm, as described in Methods. The ratio of M6G and DAMGO was determined against morphine.

In addition to its greater potency, DAMGO also had a longer duration of action, lasting almost an hour (FIG. 1a). Like morphine, peak DAMGO actions were seen immediately after removal from the DMSO solution. These analgesic responses were easily reversed by systemic naloxone (1 mg/kg s.c.), confirming the opioid selectivity of the response (FIG. 2a). Furthermore, no analgesic response with these agents was seen in the proximal portions of the tail not exposed to the opioid solutions.

To further confirm the selectivity of the method, we looked at the distribution of radioactivity following immersion into a solution containing either [$^{125}$I]morphine or [$^{125}$I]DAMGO (Table 2). The region of the tail exposed to the solution had high levels of radioactivity. A more proximal portion of the tail which was not directly exposed to the solution had levels of radioactivity <1% of those in the distal portion of the tail immersed in the solution. Furthermore, no detectable levels of radioactivity were seen in blood, brain or spinal cord.

TABLE 2

Distribution of [$^{125}$I]DAMGO following topical administration

| Tissue | Radioactivity(cpm/g) | |
|---|---|---|
| | $^{125}$I-Morphine | $^{125}$I-DAMGO |
| Blood | 69 ± 18 | <50 |
| Brain | 55 ± 26 | <50 |
| Spinal cord | 71 ± 12 | <50 |
| Tail | | |
| Exposed | 38,460 ± 3,455 | 45,280 ± 2,637 |
| Unexposed | 234 ± 51 | 157 ± 51 |

The distal part of the tail (4-4.5 cm) was immersed in [$^{125}$I]-labeled morphine or DAMGO (100 µCi/ml) in DMSO and exposed for 3 min. Brain, spinal cord, blood samples, as well as segments from the exposed and unexposed portions of the tail were obtained within 5 min of exposure, weighed and counted directly in a Packard 5500 Gamma Spectrometer. The unexposed tail was less than a 1 cm from the exposed region. Radioactivity was expressed in cpm per gram tissue (cpm/g). Results are the means ± s.e.m. of three animals for each radiolabeled drug.

EXAMPLE 3

Topical Morphine-6β-Glucuronide Analgesia Morphine-6β-glucuronide (M6G) administered locally by subcutaneous injection in the tail was analgesic, but it had a ceiling effect of 30% with doses of 10 or 30 µg (data not shown). In the topical paradigm, M6G yielded a full analgesic response with a peak effect immediately after removal from the solution (FIG. 1a) and a potency similar to that of morphine (FIG. 1b; Table 1). As with morphine, proximal tail segments did not display analgesia and the M6G response was readily reversed by systemic naloxone (FIG. 2a). The duration of M6G action following topical administration was similar to that of DAMGO and longer than those of morphine (FIG. 1a). The M6G-selective antagonist 3-methoxynaltrexone (3MeONtx) (Brown et al., 1997) also significantly lowered the M6G response (FIG. 2b). In contrast, the same 3MeONtx dose was inactive against the analgesic actions of morphine or DAMGO (FIG. 2b). In addition to supporting the selectivity of 3MeONtx for the M6G receptors, these observations strongly supported the presence of functional peripheral M6G receptors.

EXAMPLE 4

Peripheral/Central Synergy

Prior work from our laboratory has suggested a potent synergy between peripheral and central morphine systems. We also examined these interactions following topical administration. Topically, the actions of morphine rapidly dissipated, falling from 80% at 1 min to only 30% at 10 min. No analgesia was seen by 30 min. Minimally active doses of intrathecal or subcutaneous morphine markedly potentiated the response of topical morphine (FIG. 3). This is most dramatic at time points beyond 30 min, at which point the topical response alone was completely lost. At these longer time points, the analgesic responses of the combinations were significantly greater than their additive effects (FIG. 3b).

We next looked at the effects of a fixed dose of topical morphine on the $ED_{50}$ values of spinal and systemic morphine (Table 3).

TABLE 3

Effects of topical morphine on systemic and spinal morphine analgesia

| Morphine Route | $ED_{50}$ value | Topical Shift |
|---|---|---|
| Systemic alone | 4.3 mg/kg (2.9-6.4) | |
| Systemic + topical | 0.66 mg/kg (0.4-1.0) | 6.5 |
| Spinal alone | 550 ng (386-822) | |
| Spinal + topical | 46 ng (21-84) | 12 |

$ED_{50}$ values and 95% confidence limits were determined for morphine given systemically alone or in conjunction with a fixed dose of topical morphine (15 mM). Testing was done 30 mm following the treatments, at which point there were no observable effects from the topical morphine alone. $ED_{50}$ values and 95% confidence limits were determined -for morphine given intrathecally alone and with a fixed dose of topical morphine (15 mM). Testing was done 15 mm following the treatments, at which point the topical morphine had only a limited (15%) response.

Topical morphine potentiated the analgesic potency of systemic morphine almost 7-fold, even though it had no activity alone at the time point examined (30 min). Topical morphine also enhanced the potency of intrathecal morphine almost 12-fold. Thus, these results support the earlier suggestions of potentiation between peripheral and central morphine analgesic systems.

EXAMPLE 5

Peripheral Morphine Tolerance

Peripheral systems are important in the production of tolerance following systemic administration of morphine (Kolesnikov et al., 1996). The tail immersion approach permits repeated local administration of drug without tissue damage, facilitating the study of peripheral morphine tolerance. Daily topical morphine (15 mM) produced profound tolerance by the third day (FIG. 4), shifting morphine's $ED_{50}$ value over 9-fold (Table 4). Topical tolerance developed more rapidly and to a greater extent than that seen with daily systemic drug, where 5 days of treatment only shifted the morphine dose-response approximately 2-fold.

TABLE 4

Tolerance to systemic and topical morphine

| | $ED_{50}$ (95% confidence limits) | | |
|---|---|---|---|
| Morphine Treatment | Naive | Tolerant | Ratio |
| Systemic | 4.3 mg/kg (2.4-5.9) | 8.7 mg/kg (5.4, 9.7) | 2 |
| Topical | 8.3 mM (4.1-10.2) | 78 mM (49, 123) | 9.4 |

Morphine $ED_{50}$ values following either topical or systemic administration were determined in naive mice and in groups of mice which had received morphine chronically. $ED_{50}$ values and 95% confidence limits were determined using at least three doses of drug (n =10-20/dose). In the systemic group, mice received morphine (5 mg/kg, s.c.) daily for four days prior to testing while the topical group were treated with a morphine solution (15 mM) daily for two days and the $ED_{50}$ value determined morphine were used to calculate the $ED_{50}$ values.

Mice given morphine systemically showed significant tolerance to topical morphine as well as to the mu peptide DAMGO (FIG. 5). However, the analgesic activity of topical M6G in these mice remained unchanged, confirming the lack of cross tolerance reported previously (Rossi et al., 1996).

EXAMPLE 6

Blockade of Peripheral Morphine Tolerance by the NMDA Antagonists, MK 801

NMDA/nitric oxide cascade plays an important role in the production of morphine tolerance (Kolesnikov et al., 1993). Blockade of this system prevents the development of morphine tolerance without interfering with analgesia. The NMDA antagonist MK801 given systemically also prevented the development tolerance to topical morphine (FIG. 6a). Topical MK801 also blocked morphine tolerance as effectively as systemic drug (FIG. 6a), but intrathecal MK801 was ineffective. Topical MK801 actions were dose-dependent, with 0.3 mM effectively blocking tolerance (FIG. 6b).

Furthermore, topical MK801 could reverse pre-established tolerance (FIG. 6c). After treating mice with topical morphine alone for three days the analgesic response was eliminated. Adding MK801 to the treatment regimen restored analgesic sensitivity over the next two days despite the continued administration of morphine. The higher MK801 dose was slightly more effective than the lower one. The slow rate reversal with no effect after the first dose argued strongly against a simple potentiation of morphine potency.

EXAMPLE 7

Blockade of Peripheral Morphine Tolerance by the NMDA Antagonist, Ketamine

Daily topical morphine (15 mM) led to tolerance with the complete loss analgesia by the third day (FIGS. 7A and B). The NMDA receptor antagonist ketamine given systemically prevented the development of tolerance to topical morphine, but intrathecal ketamine was ineffective (data not shown). Topical ketamine co-administered with morphine blocked tolerance as effectively as systemic drug in a dose-dependent manner (FIG. 7A). The lower dose (3.6 mM) delayed the appearance of tolerance, but the higher dose (36 mM) effectively blocked tolerance. Ketamine alone had no appreciable effect in this assay.

Topical ketamine also reversed pre-established tolerance (FIG. 7B). After treating mice with a fixed concentration of topical morphine alone for three days the mice displayed no analgesia. Ketamine added to the treatment regime restored analgesic sensitivity over next three days despite the continued administration of morphine.

The ability of topical ketamine to prevent and/or reverse morphine tolerance implies a peripheral mechanism of action and is similar to the above experiment with dizocilpine (MK-801). Mechanistically, these observations are consistent with the possibility that peripheral tolerance is mediated through peripheral NMDA receptors, possibly on the same dorsal root ganglia neurons containing the opioid receptors.

Discussion

Peripheral opioid actions are becoming increasing important in our understanding of opioid actions, as demonstrated by the role of peripheral and central synergy in the actions of systemic morphine (Kolesnikov et al., 1996). Furthermore, peripheral sites of action play a major role in the development of tolerance to systemic drug. Exploring peripheral mechanisms is not simple. Earlier studies utilized local injections into the tail to examine peripheral mechanisms. Although useful, this approach has a number of disadvantages, particularly when looking at repeated dosing. In an effort to avoid this problem, we have developed a topical approach which is generally applicable to both alkaloids and peptides. The tail immersion technique has a number of advantages. Foremost is the ability to repeatedly treat the mice without tissue damage secondary to injections. The paradigm was selective for local mechanisms. Testing proximal regions of the tail failed to reveal any analgesic response, confirming the distribution studies with $^{125}$I opioid which documented the localization of the radiolabel only to the regions immersed in the drug solution and the absence of any detectable uptake into the blood or central nervous system. Equally important, DMSO alone had no effects in the tailflick assays. Presumably, the activity of this approach is not limited to DMSO and other solvents or topical creams could be used. We had not anticipated that topical solutions of peptides would be active, but a number of different mu and delta peptides are effective in this paradigm. Clearly, topical approaches open new possibilities clinically for these peptides which are not very effective systemically. Thus, the topical approach provides a useful approach for the examination of peripheral opioid mechanisms and as a therapeutic in pain management.

Peripherally, all the opioids tested were effective analgesics. Of the three, DAMGO was the most active. The similar potencies of morphine and M6G peripherally contrasts with their central actions, where M6G is approximately 100-fold more active than morphine. In all cases, the proximal segments of the tail which were not exposed to the opioid solution were not analgesic, confirming the peripheral site of action for the sites immersed in the opioid solution. The responses were readily antagonized by naloxone. Centrally, 3-MeONtx selectively reverses M6G analgesia without interfering with morphine analgesia, consistent with a different receptor mechanism of action (Brown et al., 1997). 3-MeONtx also reversed peripheral M6G analgesia without affecting either DAMGO or morphine actions. Thus, peripheral M6G analgesia showed the same antagonist selectivity as seen centrally.

Prior studies had documented synergy between peripheral and central morphine actions. The current studies confirmed these earlier observations. Combining topical morphine with morphine given either systemically or spinally revealed marked potentiation of the responses beyond those expected for simple additive interactions. Thus, if topical opioids were to be used clinically, these results would suggest that they would be most effective in combination with systemic dosing. By lowering the necessary doses of systemic drug, topical opioids might greatly diminish the side-effects currently associated with opioid analgesics.

Chronic dosing with systemic morphine treatment leads to tolerance. Localizing the site of morphine tolerance has been difficult. Mice tolerant to systemic morphine show normal sensitivities to morphine given either spinally or supraspinally (Roerig et al., 1984), but not peripherally (Kolesnikov et al., 1996). Indeed, the 19-fold shift in the local morphine dose-response curves far exceed the shift following systemic administration. Our current studies support a role for peripheral sites in morphine tolerance. Chronic topical morphine produced tolerance very rapidly, decreasing the response to undetectable levels by three days corresponding to over a 9-fold shift in the dose-response curve. Chronic dosing with DMSO alone had no effect. The rate of development of tolerance to equianalgesic doses of systemic drug was slower and to a smaller extent, shifting the dose-response curve only 2-fold after 5 days. Mice tolerant to perpiheral morphine were cross tolerant to DAMGO, but not to M6G. This lack of cross tolerance is consistent with the selective reversal of M6G analgesia by 3-MeONtx and is consistent with a unique receptor mechanism of M6G action.

N-Methyl-D-aspartate (NMDA) receptor antagonists or nitric oxide synthase (NOS) inhibitors prevent the production of morphine tolerance (Trujillo and Akil, 1994; Gutstein and Trujillo, 1993; Ben-Eliyahu et al., 1992; Kolesnikov et al, 1993). In view of the importance of peripheral opioid mechanisms in tolerance in these paradigms, we looked at the role of peripheral NMDA antagonists. Topical morphine tolerance was effectively blocked by MK801 given systemically or topically, but not spinally. Systemic MK801 would be expected to have access throughout the animal, including peripheral sites, while the intrathecal drug would be restricted to central sites. Likewise, topical ketamine prevented and/or reversed morphine tolerance. Thus, only treatments with access to peripheral sites were active in this model, implying that peripheral NMDA receptors are responsible for mediating topical morphine tolerance. Recent evidence supports the presence of excitatory amino acid (EAA) receptors on peripheral cutaneous axons (Carlton et al., 1995; Davidson et al., 1997; Zhou et al., 1996). Additional studies are needed to verify the site of action. However, the activity of topical NMDA antagonists opens many clinical possibilities in pain management. Many of the current NMDA receptor antagonists are not suitable for clinical use due to profound psychomimetic side-effects. Restricting their use to topical formulations may provide a way of utilizing their ability to interfere with tolerance development without producing limiting side-effects.

Peripheral opioids clearly have important roles in analgesia and tolerance. The ability of topical opioids to produce analgesia alone and potentiate systemic drugs offers a new approach which may prove useful clinically. The activity of topical peptides further enhances this approach since it opens the way for many highly selective agents acting through non-mu opioid receptor mechanisms. Finally, the ability to block topical tolerance with peripherally acting NMDA antagonists is another exciting advance in the clinical treatment of pain.

REFERENCES

Barber, A and Gottschlich, R (1992) Opioid agonists and antagonists: an evaluation of their peripheral actions in inflammation. *Med Res Reviews* 12:525-562.

Ben-Eliyahu, S, Marek, P, Vaccarino, A L, Mogil, J S, Sternberg, W F and Liebeskind, J C (1992) The NMDA receptor antagonist MK-801 prevents long-lasting non-associative morphine tolerance in the rat. *Brain Res* 575:304-308.

Brown, G P, Yang, K, King, M A, Rossi, G C, Leventhal, L, Chang, A and Pasternak, G W (1997) 3-Methoxynaltrexone, a selective heroin/morphine-6β-glucuronide antagonist. *FEBS Lett* 412:35-38.

Carlton, S M, Hargett, G L and Coggeshall, R E (1995) Localization and activation of glutamate receptors in unmyelinated axons of rat glabrous skin. *Neurosci Lett* 197:25-28.

Chien, C-C, Carroll, F I, Brown, G P, Pan, Y-X, Bowen, W and Pasternak, G W (1997) Synthesis and characterization of [$^{125}$I]3'(−)-iodopentazocine, a selective $\sigma_1$ receptor ligand. *Eur J Pharmacol* 321:361-368.

Dahl, M R, Dasta, J F, Zuelzer, W and McSweeney, T D (1990) Lidocaine local anesthesia for arthroscopic knee surgery. *Anesth Analg* 71:670-674.

Dalsgaard, J, Felsby, S, Juelsgaard, P and Froekjaer, J (1994) Low-dose intra-articular morphine analgesia in day case knee arthroscopy: A randomized double-blinded prospective study. *Pain* 56:151-154.

Davidson, E M, Coggeshall, R E and Carlton, S M (1997) Peripheral NMDA and non-NMDA glutamate receptors contribute to nociceptive behaviors in the rat formalin test. *Neuroreport* 8:941-946.

Gutstein, H B and Trujillo, K A (1993) MK-801 inhibits the development of morphine tolerance at spinal sites. *Brain Res* 626:332-334.

Heard, S O, Edwards, T, Ferrari, D, Hanna, D, Wong, P D, Liland, A and Willock, M M (1992) Analgesic effect of intraarticular bupivacaine or morphine after arthroscopic knee surgery: a randomized, prospective, double-blind study. *Anesth Analg* 74:822-826.

Joris, J L, Dubner, R and Hargreaves, K M (1987) Opioid analgesia at peripheral sites: a target for opioids released during stress and inflammation? *Anesth Analg* 66:1277-1281.

Junien, J L and Wettstein, J G (1992) Role of opioids in peripheral analgesia. *Life Sci* 51:2009-2018.

Khoury, G F, Chen, ACN, Garland, D E and Stein, C (1992) Intraarticular morphine, bupivacaine, and morphine/bupivacaine for pain control after knee videoarthroscopy. *Anesthesiology* 77:263-266.

Kolesnikov, Y A, Jain, S, Wilson, R and Pasternak, G W (1996) Peripheral morphine analgesia: Synergy with central sites and a target of morphine tolerance. *J Pharmacol Exp Ther* 279:502-506.

Kolesnikov, Y A, Pick, C G, Ciszewska, G and Pasternak, O W (1993) Blockade of tolerance to morphine but not to kappa opioids by a nitric oxide synthase inhibitor. *Proc Natl Acad Sci USA* 90:5162-5166.

Mays, K S, Lipman, J J and Schnapp, M (1987) Local analgesia without anesthesia using peripheral perineural morphine injections. *Anesth Analg* 66:417-420.

Pick, C G, Nejat, R and Pasternak, G W (1993) Independent expression of two pharmacologically distinct supraspinal mu analgesic systems in genetically different mouse strains. *J Pharmacol Exp Ther* 2265:166-171.

Raja, S N, Dickstein, R E and Johnson, C A (1992) Comparison of postoperative analgesic effects of intraarticular bupivacaine and morphine following arthroscopic knee surgery. *Anesthesiology* 77:1143-1147.

Reisine, T and Pasternak, G W (1996) Opioid analgesics and antagonists. In Goodman & Gilman's: The Pharmacological Basis of Therapeutics, ed. by J G Hardman and L E Limbird, pp. 521-556, McGraw-Hill.

Roerig, S C, O'Brien, S M, Fujimoto, J A and Wilcox, G L (1984) Tolerance to morphine analgesia: decreased multiplicative interaction between spinal and supraspinal sites. *Brain Res* 308:360-363.

Rossi, G C, Brown, G P, Leventhal, L, Yang, K and Pasternak, G W (1996) Novel receptor mechanisms for heroin and morphine-6β-glucuronide analgesia. *Neurosci Lett* 216:1-4.

Stein, C (1993) Peripheral mechanisms of opioid analgesia. *Anesth Analg* 76:182-191.

Stein, C, Schafer, M and Hassan, AHS (1995) Peripheral opioid receptors. *Ann Med* 27:219-221.

Trujillo, K A and Akil, H (1994) Inhibition of opiate tolerance by non-competitive N-methyl-D-aspartate receptor antagonists. *Brain Res* 633:178-188.

Zhou, S, Bonasera, L and Carlton, S M (1996) Peripheral administration of NMDA, AMPA or KA results in pain behaviors in rats. *Neuroreport* 7:895-900.

We claim:

1. A topical pharmaceutical composition comprising ketamine in a tolerance-attenuating dosage, morphine and a pharmaceutically acceptable topical excipient effectively delivering the ketamine and morphine to local peripheral receptors and not to central receptors, wherein the dosage of ketamine is within a tolerance-attenuating range sufficient to yield a dose-lowering effect on the morphine such that the concentration of morphine necessary to provide effective analgesia is within a range of about 1.0 to about 10% by weight of the composition.

2. The topical pharmaceutical composition according to claim 1, further comprising a local anesthetic.

3. The topical pharmaceutical composition according to claim 2, wherein the local anesthetic is selected from the group consisting of lidocaine, bupivacaine, mepivacaine, ropivacaine, tetracaine and benzocaine.

4. The topical pharmaceutical composition according to claim 1, wherein the pharmaceutically acceptable topical excipient is in the form of an aqueous excipient.

5. The topical pharmaceutical composition according to claim 1, wherein the pharmaceutically acceptable topical excipient is in the form of a gel excipient.

6. A topical pharmaceutical composition comprising ketamine and morphine and a topical excipient effectively delivering the ketamine and morphine to local peripheral opiate receptors and not to central opiate receptors and wherein the excipient is condensation products of an alkylene oxide with fatty acids, aloe vera, DMSO, lecithin, lecithine base, or propylene glycol, and the dosage of ketamine is within a tolerance-attenuating range sufficient to yield a dose-lowering effect on the morphine such that the concentration of morphine necessary to provide effective analgesia is within a range of about 1.0 to about 10% by weight of the composition.

7. The topical pharmaceutical composition according to claim 6, further comprising a local anesthetic.

8. The topical pharmaceutical composition according to claim 7, wherein the local anesthetic is selected from the group consisting of lidocaine, bupivacaine, mepivacaine, ropivacaine, tetracaine and benzocaine.

9. A method of providing peripheral analgesia and not central or systemic analgesia to a mammal comprising topically administering a tolerance-attenuating dose of ketamine prior to, concurrently with, or following topically administering morphine, wherein the morphine and ketamine function through local peripheral receptors and not central receptors, wherein the administration is by topical application of an aqueous solution, gel, lotion, ointment, cream or spray and the dosage of ketamine is within a tolerance-attenuating range sufficient to yield a dose-lowering effect on the morphine such that the concentration of morphine necessary to provide effective analgesia is within a range of about 1.0 to about 10% by weight of the composition.

10. The method according to claim 9, wherein ketamine is administered in a dose of about 0.1% to about 5%, by weight, of total weight of ketamine and morphine.

11. A method of providing tolerance attenuating analgesia to a mammal with pre-existing tolerance to an analgesic comprising topically administering a tolerance-attenuating dose of ketamine concurrently or following topically administering morphine, wherein the morphine and ketamine function through local peripheral receptors and not central receptors, wherein the administration is by topical application of an aqueous solution, gel, lotion, ointment cream or spray and the dosage of ketamine is within a tolerance-attenuating range sufficient to yield a dose-lowering effect on the morphine such that the concentration of analgesic necessary to provide effective analgesia is within a range of about 1.0 to about 10% by weight of the composition.

12. The method according to claim 9, wherein the administration is by topical application of an aqueous solution.

13. The method according to claim 11, wherein the administration is by topical application of an aqueous solution.

* * * * *